(12) United States Patent
Sartor et al.

(10) Patent No.: US 10,543,256 B2
(45) Date of Patent: Jan. 28, 2020

(54) STABLE PHARMACEUTICAL FORMULATION COMPRISING A RECONSTITUTED PULMONARY SURFACTANT COMPOSITION

(71) Applicant: CHIESI FARMACEUTICI S.P.A., Parma (IT)

(72) Inventors: Franco Sartor, Parma (IT); Marisa Pertile, Parma (IT); Annamaria Soliani Raschini, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

(21) Appl. No.: 15/683,822

(22) Filed: Aug. 23, 2017

(65) Prior Publication Data
US 2018/0055914 A1    Mar. 1, 2018

(30) Foreign Application Priority Data
Aug. 24, 2016 (EP) .................................. 16185516

(51) Int. Cl.
*A61K 38/17* (2006.01)
*A61K 31/685* (2006.01)
(52) U.S. Cl.
CPC .......... *A61K 38/395* (2013.01); *A61K 31/685* (2013.01)
(58) Field of Classification Search
CPC combination set(s) only.
See application file for complete search history.

(56) References Cited

U.S. PATENT DOCUMENTS

| | | | | |
|---|---|---|---|---|
| 5,876,970 A | * | 3/1999 | Benson ............... | C07K 14/785 435/69.1 |
| 6,284,804 B1 | * | 9/2001 | Singh .................. | A61K 9/0043 424/78.04 |
| 2014/0142021 A1 | * | 5/2014 | Johansson ............ | C07K 14/785 514/1.5 |
| 2018/0298057 A1 | * | 10/2018 | Koval .................... | C07K 7/06 |

FOREIGN PATENT DOCUMENTS

| | | |
|---|---|---|
| EP | 0 976 403 | 2/2000 |
| WO | 2008/044109 | 4/2008 |
| WO | 2010/139442 | 12/2010 |
| WO | WO-2010139442 A1 * | 12/2010 ........... C07K 14/785 |

OTHER PUBLICATIONS

Taha (Buffers and Ionic Salts: Densities and Solubilities of Aqueous and Electrolyte Solutions of Tris(hydroxymethyl)aminomethane and N-Tris[hydroxymethyl]-4-amino-butanesulfonic Acid, J. Chem. Eng. Data 2009, 54, 2501-2512) (Year: 2009).*
EMBL (Protein Purification Extraction and Clarification Choice of lysis buffer and additives, Oct. 31, 2014) (Year: 2014).*
Taha (Buffers and Ionic Salts: Densities and Solubilities of Aqueous and Electrolyte Solutions of Tris(hydroxymethyl)aminomethane and N-Tris[hydroxymethyl]-4-amino-butanesulfonic Acid, J. Chem. Eng. Data 2009, 54, 2501-2512, of record) (Year: 2009).*
EMBL (Protein Purification Extraction and Clarification Choice of lysis buffer and additives, Oct. 31, 2014, of record) (Year: 2014).*
International Search Report and Written Opinion dated Oct. 19, 2017 in Corresponding PCT/EP2017/070169 filed Aug. 9, 2017.
European Search Report in Application No. 16185516.8 dated Feb. 3, 2017.

* cited by examiner

*Primary Examiner* — Karlheinz R. Skowronek
*Assistant Examiner* — Khalid Kader
(74) *Attorney, Agent, or Firm* — Oblon, McClelland, Maier & Neustadt, L.L.P.

(57) ABSTRACT

Physically and chemically stable pharmaceutical formulations in the form of an aqueous suspension comprising a reconstituted pulmonary surfactant are useful for the prophylaxis and/or treatment of respiratory distress syndrome (RDS) and other respiratory disorders.

14 Claims, No Drawings

Specification includes a Sequence Listing.

STABLE PHARMACEUTICAL FORMULATION COMPRISING A RECONSTITUTED PULMONARY SURFACTANT COMPOSITION

CROSS REFERENCES TO RELATED APPLICATIONS

This application claims priority to European Patent Application No. 16185516.8, filed on Aug. 24, 2016, which is incorporated herein by reference in its entirety.

BACKGROUND OF THE INVENTION

Field of the Invention

The present invention relates to stable pharmaceutical formulations in the form of an aqueous suspension comprising a reconstituted pulmonary surfactant. The present invention also relates to the prophylaxis and/or treatment of respiratory distress syndrome (RDS) and other respiratory disorders by administering such a formulation.

Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

Lung surfactant complex is composed primarily of lipid and contains minor amounts of various proteins. An absence of adequate levels of this complex results in malfunction of the lung. This syndrome is called Respiratory Distress Syndrome (RDS) and it commonly affects preterm infants.

Said syndrome is effectively treated with commercially available modified natural surfactant preparations extracted from animal lungs, such as the gold standard preparation known as Curosurf®.

The main constituents of these surfactant preparations are phospholipids and surfactant hydrophobic proteins B and C (SP-B and SP-C).

Due to the drawbacks of the surfactant preparations from animal tissues, such as the complication of the production process, and possible viral contamination and/or induction of immune reactions, synthetic surfactants have been made available.

Said synthetic surfactants can be simply mixtures of synthetic compounds, primarily phospholipids and other lipids and are known as "artificial" surfactants; although they have been used in clinical practice for many years, their efficacy is not comparable to that of modified natural surfactant.

Artificial surfactants also containing surfactant proteins/peptides are also currently under development. They are termed either "reconstituted" surfactants or "bio-mimetic surfactants".

Reconstituted surfactants comprising both SP-B and SP-C analogues resembling human surfactant proteins have been disclosed, for example in WO 00/76535, WO 2008/011559, and WO 2008/044109, all of which are incorporated herein by reference in their entireties.

A particular reconstituted surfactant has been disclosed in WO 2010/139442, which is incorporated herein by reference in its entirety, and quoted in the literature as CHF 5633.

CHF 5633 contains:

a) 1.5% by weight of a polypeptide analog of the native surfactant protein SP-C with the sequence IPSSPVHLKRLKLLLLLLLLILLLILGALLLGL (SEQ. ID:NO. 1);

b) 0.2% by weight of a polypeptide analog of the native surfactant protein SP-B with the sequence CWLCRALIKRIQALIPKGGRLLPQLVCRLVLRCS (SEQ. ID:NO. 2);

c) about 49.15% by weight of 1,2-dipalmitoyl-sn-glycero-3-phosphocholine (DPPC); and d) about 49.15% by weight of the sodium salt of 1-palmitoyl-2-oleyl-sn-glycero-3-phosphoglycerol (POPG);

all the amounts being calculated on the total weight of the reconstituted surfactant.

CHF 5633 is prepared by admixing the polypeptides and the phospholipids in the presence of a mixture of ethanol and chloroform, then by removing the organic solvents by evaporation under vacuum. Said method affords a concentrated suspension in an aqueous medium (up to 80 mg/ml) of low viscosity (not more than 20 mPas, preferably less than 15 mPas at 25° C.), wherein the surfactant is in form of highly dispersed mixture of liposomal vesicles, i.e. multilamellar vesicles (MLV), giant unilamellar vesicles (GUV), large unilamellar vesicles (LUV) and small unilamellar vesicles (SUV), prevalently MLV.

The possibility of preparing a concentrated suspension in a small volume is indeed a feature of particular importance for its clinical use.

The above aqueous suspension of CHF 5633, upon single intratracheal administration at a total concentration of 80 mg/ml to pre-term neonates, turned out to be safe and efficacious.

On the other hand, besides good efficacy, the above surfactant composition should also fulfil the requirement of adequate shelf-life suitable for commercial distribution, storage and use.

Therefore, the above formulation should exhibit at least the same chemical and physical stability of modified natural surfactants such as Curosurf®, i.e. at least 18 months at 5° C.

Example 2 of WO 2010/139442, which is incorporated herein by reference in its entirety, reports that a formulation in the form of a simple aqueous suspension is physically chemically stable after 6 months of storage at 5° C.

In this context the expression physically stable means inter alia that the viscosity does not substantially change over time.

However, it was observed that for a period longer than 6 months, the viscosity tends to increase up to values of about 50 mPas at 25° C.

In the literature, it was reported that the hydrolysis of phospholipids reaches a minimum at a pH around neutrality and that it could be affected by buffer species.

WO 92/22315 and WO 2010/139442, which are incorporated herein by reference in their entireties, generically disclosed that synthetic pulmonary surfactant formulated as a liquid suspension could contain small amounts of auxiliary substances such as pH buffering agents.

However, although the prior art provides some generic indication about chemical stability of phospholipids-based surfactants, no document discloses the specific conditions to obtain a pulmonary surfactant composition comprising phospholipids in combination with synthetic analogs of the SP-C and SP-B proteins of adequate chemical and physical stability for pharmaceutical use, i.e. for at least 18 months at 5° C.

Thus, there remains a need for pulmonary surfactant compositions which exhibit improved stability.

SUMMARY OF THE INVENTION

Accordingly, it is one object of the present invention to provide novel pulmonary surfactant compositions.

It is another object of the present invention to provide novel pulmonary surfactant compositions which are stable.

It is another object of the present invention to provide novel methods for the prophylaxis and/or treatment of respiratory distress syndrome (RDS) and other respiratory disorders by administering such a formulation.

These and other objects, which will become apparent during the following detailed description, have been achieved by the inventors' discovery of the formulations described below.

Thus, the present invention provides propellant-free, ready-to-use pharmaceutical formulations in the form of aqueous suspension comprising:

a) from 1.02 to 1.32 mg/ml of a polypeptide analog of the native surfactant protein SP-C with the sequence IPSSPVHLKRLKLLLLLLLLILLLILGALLLGL (SEQ. ID:NO. 1);

b) from 0.136 to 0.176 mg/ml of a polypeptide analog of the native surfactant protein SP-B with the sequence CWL-CRALIKRIQALIPKGGRLLPQLVCRLVLRCS (SEQ. ID:NO. 2);

c) from 33.42 to 43.25 mg/ml of 1,2-dipalmitoyl-sn-glycero-3-phosphocholine (DPPC);

d) from 33.42 to 43.25 mg/ml of the sodium salt of 1-palmitoyl-2-oleyl-sn-glycero-3-phosphoglycerol (POPG Na);

e) from 0.5 to 3.5 mg/ml of a buffer agent selected from the group consisting of tris(hydroxymethyl)aminomethane hydrochloride or a phosphate-buffer; and f) a tonicity agent in an amount sufficient to provide an osmolarity of from about 250 to about 400 mosm/l;

wherein the pH is comprised between 6.4 and 7.6.

In a second aspect, the present invention provides the use of such a pharmaceutical formulation for the manufacture of a medicament for the prophylaxis and/or treatment of respiratory distress syndrome (RDS) and other respiratory disorders.

The present invention also provides a method for the prophylaxis and/or treatment of respiratory distress syndrome (RDS) and other respiratory disorders, said method comprising the administration, to a patient in need thereof, of a therapeutically effective amount of such a pharmaceutical formulation.

The present invention also provides a kit comprising: a) a composition of the invention in a powder form in a first unit dosage form; b) a pharmaceutically acceptable carrier in a second unit dosage form; and c) container means for containing said first and second dosage forms.

Further, the present invention provides a method for avoiding the increase of the viscosity during storage of a pharmaceutical formulation in form of aqueous suspension of reconstituted pulmonary surfactant composition comprising phospholipids in combination with synthetic analogs of the SP-C and SP-B proteins, said method comprising the adjustment of the pH between 6.4 and 7.6 with a suitable buffer agent.

DETAILED DESCRIPTION OF THE PREFERRED EMBODIMENTS

"Surfactant activity" for a surfactant preparation is defined as the ability to lower the surface tension.

The in vitro efficacy of exogenous surfactant preparations is commonly tested by measuring its capability of lowering the surface tension using suitable apparatus such as Wilhelmy Balance and Captive Bubble Surfactometer.

The in vivo efficacy of exogenous surfactant preparations is commonly tested by measuring two parameters: i) the tidal volume that is an index of the lung compliance, and ii) the lung gas volume which is an index of the alveolar air expansion or patency at the end of expiration, and hence of the capability of forming a stable phospholipid film in the alveoli at the end of expiration.

A "therapeutically effective" amount as used herein refers to an amount of reconstituted pulmonary surfactant capable of preventing, avoiding, reducing or eliminating the respiratory disease or disorders associated with the lack or dysfunction of endogenous surfactant.

The term "pharmaceutically acceptable" or "physiologically tolerable" refers to compositions, medium, solvents, salts capable of being administered to a human without the production of undesirable physiological effects.

"Polypeptide," "peptide," and "protein" are used interchangeably to refer to a polymer of amino acid residues.

The amino acid sequences are shown according to the one-letter code with the amino acid which carries the free amino group at the left end (amino terminus) and the amino acid which carries the free carboxyl group at the right end (carboxy terminus).

All the amino acid residues identified herein are in the natural L-configuration. The meaning of the one-letter code for amino acids is reported for instance in WO 2008/044109, which is incorporated herein by reference in its entirety.

The term "polypeptide analogue of the native surfactant protein SP-C" means a polypeptide having an amino acid sequence in which, compared to the native SP-C protein, amino acids are missing and/or have been replaced by other amino acids, so long as the polypeptide, in a mixture with phospholipids, shows pulmonary surfactant activity (as demonstrable by in vitro and in vivo efficacy assays).

The term "polypeptide analogue of the native surfactant protein SP-B", means a polypeptide having an amino acid sequence in which, compared to the native SP-B protein, amino acids are missing and/or have been replaced by other amino acids so long as the polypeptide, in a mixture with phospholipids, shows pulmonary surfactant activity (as demonstrable by in vitro and in vivo efficacy assays).

"Recombinant" when used with reference, e.g., to a cell, or nucleic acid, protein, or vector, indicates that the cell, nucleic acid, protein or vector, was modified by the introduction of a heterologous nucleic acid or protein or the alteration of a native nucleic acid or protein.

The term "about" applied to a value, indicates a variability of ±1%.

The term "phospholipids" indicate lipids in which one fatty acid was replaced by a phosphate group and a simple organic molecule. The most common class of phospholipids that can be found in surfactant preparations are: phosphatidylcholines (PC), phosphatidylethanolamine (PE) phosphatidylglycerol (PG), phosphatidylinositol (PI), and phosphatidylserine (PS).

The glycerol moieties of the phospholipids are mainly esterified with long chain fatty acids which in turn can be saturated (e.g. myristic, palmitic and stearic acid), monounsaturated (e.g. oleic acid) or polyunsaturated (e.g. linoleic and arachidonic acid). In particular, the species taken into consideration in the application are:

1,2-dipalmitoyl-sn-glycero-3-phosphocholine, also known as dipalmitoyl-phosphatidylcholine (DPPC), which is a saturated derivative, and 1-palmitoyl-2-oleyl-sn-glycero-3-phosphoglycerol, also known as palmitoyl-oleyl-phosphatidylglycerol (POPG) which is a monounsaturated derivative.

In the present application, the particle size of the vesicles is expressed in terms of volume diameter, in particular in terms of d(v,50) which corresponds to the volume of 50 percent by weight of the particles.

Said particle size could be quantified by known techniques such as laser diffraction or single particle optical sizing.

The term "phosphate-buffer" refers to pharmaceutically acceptable buffer agents, widely used in biological applications, having for instance one of the following compositions: $Na_2HPO_4$ heptahydrate, and $NaH_2PO_4$ monohydrate, or $Na_2HPO_4$ dihydrate, and $NaH_2PO_4$ dihydrate, or NaCl, KCl, $Na_2HPO_4$, and $KH_2PO_4$ (hereinafter PBS) or NaCl, $Na_2HPO_4$ heptahydrate, and $NaH_2PO_4$ monohydrate.

Said buffers have a $pKa_2$ around of 7.2 at 25° C. and their best buffer capacity is in the range of pH 6.5-8.0.

"Tris(hydroxymethyl)aminomethane hydrochloride" also known as 2-amino-2-hydroxymethyl-propane-1,3-diol hydrochloride or TRIS is a pharmaceutically acceptable buffer agent, widely used in biological applications.

TRIS has a pKa of 8.06 at 25° C. and its best buffer capacity is the range of pH 7.2-8.5.

The present invention is based in part on the unexpected finding that it is possible to avoid the increase of the viscosity during storage of a pharmaceutical formulation in the form of an aqueous suspension of a reconstituted pulmonary surfactant composition comprising phospholipids in combination with synthetic analogs of the SP-C and SP-B proteins.

While it is very well known that the pH has an effect on the hydrolysis kinetics of the phospholipids, it has been found that the control of the pH is also essential to keep low the viscosity of said reconstituted pulmonary surfactants during storage. It is also known that the initial viscosity of phospholipids aqueous suspensions is dependent on the particle size distribution and shape of the vesicles, which, in turn depends on the process applied for the manufacturing of the pulmonary surfactant.

Therefore, it was also found that, once the vesicles are formed, to avoid variation of their sizes and shape during storage, it is essential to strictly control the type and the amount of the buffer agent.

In particular, the amount of buffer should be neither too high to avoid fusion or precipitation phenomena of the vesicles nor too low to decrease its buffering capacity.

Accordingly, in one embodiment, the present invention is directed to a propellant-free, ready-to-use pharmaceutical formulation in form of aqueous suspension comprising:

a) from 1.02 to 1.32, preferably 1.2 mg/ml, of a polypeptide analogue of the native surfactant protein SP-C with the sequence (SEQ. ID:NO. 1)
IPSSPVHLKRLKLLLLLLLLILLLILGALLLGL;

b) from 0.136 to 0.176 mg/ml, preferably 0.16 mg/ml of a polypeptide analogue of the native surfactant protein SP-B with the sequence (SEQ. ID:NO. 2)
CWLCRALIKRIQALIPKGGRLLPQLVCRLVLRCS;

c) from 33.42 to 43.25 mg/ml, preferably 39.32 mg/ml, of 1,2-dipalmitoyl-sn-glycero-3-phosphocholine (DPPC);

d) from 33.42 to 43.25 mg/ml, preferably 39.32 mg/ml, of the sodium salt of 1-palmitoyl-2-oleyl-sn-glycero-3-phosphoglycerol (POPG Na);

e) from 0.5 to 3.5 mg/ml of a buffer agent selected from the group consisting of tris(hydroxymethyl)aminomethane hydrochloride or phosphate-buffer; and f) a tonicity agent in an amount sufficient to provide an osmolarity of from about 250 to about 400 mosm/l;

wherein the pH is comprised between 6.4 and 7.6.

The above formulation turned out to be physically and chemically stable for at least 18 months at 5° C., and unexpectedly no increase of the viscosity was observed.

Furthermore, said formulation remains readily re-dispersible for a prolonged period, and upon re-dispersion, does not flocculate so quickly as to prevent reproducing dosing of the active ingredients.

The polypeptide of SEQ ID:NO. 1 has also been identified in the art as SPC-33(leu), while the polypeptide of SEQ ID:NO. 2 has also been identified as Mini-B(leu).

In a preferred embodiment, the polypeptide of SEQ ID:NO2 is in the form of disulfide linked molecule wherein the intramolecular disulfide linkages are between the two cysteine residues at the 1- and 33-positions and/or between the two cysteine residues at the 4- and 27-positions.

Said polypeptide has also been identified in the art as oxidized Mini-B(leu).

Advantageously, both polypeptides may be present in the form of pharmaceutically acceptable salts. Said salts include, for example, salts of hydrochloric acid, acetic acid and trifluoroacetic acid.

Preferably, both polypeptides are present in the composition in the form of acetates.

The sodium salt of 1-palmitoyl-2-oleyl-sn-glycero-3-phosphoglycerol (POPG) may be advantageously present in the form of an equivalent pharmaceutically acceptable salt, for example the potassium salt. The corresponding relative amount could easily be determined by the person skilled in the art.

The above formulation should have an osmolarity of from about 250 to about 400 mosm/l, preferably of from 280 mosm/l to 380 mosm/l, more preferably of from 300 mosm/l to 350 mosm/l.

Advantageously, the tonicity agent is selected from the group consisting of dextrose, mannitol, sorbitol potassium chloride and sodium chloride.

Preferably, the tonicity agent is sodium chloride in a concentration of 9 mg/ml.

The pH of the formulation is from 6.4 to 7.6, preferably 6.5 to 7.5, more preferably 6.8 to 7.4, even more preferably 6.9 to 7.2.

The pH may be determined according to well-known methods and the estimated values should be taken into consideration the experimental error, usually ±0.2 units.

Advantageously, the buffer agent is selected from tris (hydroxymethyl)aminomethane hydrochloride (TRIS) or a phosphate-buffer.

Advantageously, the amount of the buffer agent is from 0.5 mg/ml to 3.5 mg/ml, preferably 0.6 to 3.0 mg/ml, corresponding to 5-20 mmol, preferably 10 mmol.

Advantageously, the phosphate buffer agent could be utilized in a concentration of 0.6 to 2.8 mg/ml.

In one embodiment of the present invention, the phosphate buffer is a phosphate-buffered saline (PBS)

In a more preferred embodiment, the buffer agent may be made of $Na_2HPO_4$ heptahydrate, and $NaH_2PO_4$ monohydrate, or $Na_2HPO_4$ dihydrate, and $NaH_2PO_4$ dihydrate.

In the case of the phosphate buffer agent, the amount is calculated without taking into the account the extent of hydration of the salts forming said buffer.

The correspondence between the concentration of the buffer agent in mg/ml and mmol could easily be determined by the person skilled in the art.

The person skilled in the art shall also properly adjust the relative amounts of the two phosphate species in order to achieve the desired pH within the claimed interval.

Advantageously, the viscosity of the formulation of the invention is less than 10 mPas (1 mPas corresponds to 1 cP), preferably less than 8 mPas, at 37° C. The viscosity is less than 15 mPas, preferably less than 10 mPas, at 25° C. The viscosity does not significantly vary during storage.

The viscosity can be determined with a common viscometer available on the market according to known methods.

The particle size of the vesicles is from 1 to 25 microns, preferably with a d(v,50) of from 8 to 15 microns, as determined with the Accusizer 780 AD apparatus (Tee Hai Chem Pte Ltd, Singapore).

The polypeptides of SEQ ID:NO. 1 and SEQ ID:NO. 2 may be prepared according to known synthetic methods or known recombinant techniques.

An excellent summary of the techniques available may be found in J. M. Steward and J. D. Young, "Solid Phase Peptide Synthesis", W.H. Freeman Co., San Francisco, 1969, and J. Meienhofer, Hormonal Proteins and Peptides", Vol. 2, p. 46, Academic Press (New York), 1983, which are incorporated herein by reference in their entireties, for solid phase peptide synthesis, and E. Schroder and K. Kubke, "The Peptides", Vol. 1, Academic Press (New York), 1965, which is incorporated herein by reference in its entirety, for classical solution synthesis.

The polypeptides may preferably be prepared using the solid-phase synthetic technique initially described by Merrifield, in J. Am. Chem. Soc. 85: 2149-2154 (1963), which is incorporated herein by reference in its entirety. Other polypeptide synthesis techniques may be found, for example, in M. Bodanszky et al., Peptide Synthesis, John Wiley & Sons, $2^{nd}$ Ed., (1976), which is incorporated herein by reference in its entirety, as well as in other known reference works.

Appropriate protective groups for use in such syntheses may be found in the above texts as well as in J. F. W. McOmie, Protective Groups in Organic Chemistry, Plenum Press, New York, N.Y. (1973), which is incorporated herein by reference in its entirety.

For example, both polypeptides may be prepared as described in WO 2008/044109, which is incorporated herein by reference in its entirety.

Effective doses of the reconstituted surfactant formulation of the invention for the treatment of a disease such as RDS, as described hereafter, vary depending upon many different factors, including type of the disease, means of administration, weight and physiological state of the patient, and whether the treatment is prophylactic or therapeutic.

In general, the dose ranges from 0.01 mg to 10 g per kg of body weight, preferably from 0.1 to 1 g per kg of body weight and the frequency of administration can vary depending on whether the treatment is prophylactic or therapeutic. Typically, a dose of about 50 mg/kg, 100 mg/kg, or 200 mg/kg is administered in one dose. For use in newborns, one or two administrations are generally sufficient.

Although needs can vary depending on the severity of the respiratory disease and/or other variables, the determination of the optimal ranges for effective dosages may be easily determined by the skilled practitioner.

The formulations may be presented in unit-dose or multi-dose containers, for example sealed ampoules and vials, or may be stored in a frozen or freeze-dried (lyophilized) condition requiring only the addition of sterile liquid carrier immediately prior to use.

Preferably, the formulation of the present invention is supplied as sterile aqueous suspension in single-use glass vials.

The overall concentration of the polypeptides a) and b) and the phospholipids c) and d) is typically in the range of from 20 mg/ml to 100 mg/ml. When formulated as single vial, it is preferably of 80 mg/ml.

The reconstituted pulmonary surfactant present in the pharmaceutical formulation of the present invention may be prepared according to conventional techniques in the pharmaceutical industry. Such techniques include the step of admixing the polypeptides and the phospholipids in the presence of an organic solvent. The solvent is then removed by dialysis, or evaporation under nitrogen and/or exposure to vacuum or by other known appropriate techniques, such as lyophilization.

Preferably, said reconstituted pulmonary surfactant is prepared by admixing the polypeptides and the phospholipids in the presence of chloroform and ethanol in a 98:2 ratio (v/v), then removing both solvent by evaporation under nitrogen.

The obtained powder is then uniformly and intimately brought into association with the liquid carrier.

The mixture of polypeptides and phospholipids can be sterilized before removing the solvent for example by sterile filtration. In certain other embodiments, the reconstituted surfactant composition is finally sterilized according to known methods.

The administration of the formulation of the present invention is carried out in a known manner, e.g. by intratracheal installation (infusion or bolus or through a catheter).

As disclosed herein, the surfactant formulation is typically used for "bolus" type administrations, either alone or optionally in conjunction with other compounds or compositions for the treatment of respiratory diseases or disorders. For example, if a subject is being treated for a respiratory disorder caused by a bacterial infection, then the reconstituted surfactant of the invention may be administered in conjunction with another compound used to treat the bacterial infection, such as an antibiotic.

Otherwise, in certain cases, for example for preventing complications such as broncho-pulmonary dysplasia, the reconstituted surfactant of the present invention may be administered in conjunction with corticosteroids such as budesonide and beclometasone dipropionate.

The composition of the present invention and the re-suspension carrier may be separately packed at the same time in a suitable container mean. Such separate packaging of the components in a suitable container mean is also described as a kit.

Therefore, the present invention is also directed to a kit, comprising: a) the composition of the present invention in a powder form in a first unit dosage form; b) a pharmaceutically acceptable carrier in a second unit dosage form; and c) container means for containing said first and second dosage forms.

A variety of methods for administering the formulations of the invention are known.

Depending on the type of disease e.g., an infant or adult with respiratory distress syndrome, different treatment methods can be appropriate.

Typically, the formulation of the present invention is administered by endotracheal instillation to patients (e.g. pre-term infants) kept under continuous or intermittent positive pressure ventilation (IPPV).

Alternatively, the surfactant may be administered by the use of a thin catheter placed in the trachea and the patient respiration supported with through specially designed nasal devices such as masks, prongs or tubes according to methodology known as nasal Continuous Positive Airway Pressure (nCPAP).

The latter approach would be only possible with a surfactant having low viscosity, as a high viscosity would make the passage of the surfactant through the thin catheter more difficult.

The formulation of the present invention is suitable to prevent, delay, alleviate, arrest or inhibit development of the symptoms or conditions associated with a respiratory disease.

In particular, it is useful for the prophylaxis and/or treatment of respiratory distress syndrome (RDS) in prematurely born babies or other diseases related to a surfactant-deficiency or dysfunction including acute lung injury (ALI), RDS in adults (ARDS), meconium aspiration syndrome (MAS), and broncho-pulmonary dysplasia (BPD).

It may also be useful for the prophylaxis and/or treatment of other respiratory disorders such as chronic obstructive pulmonary disease (COPD), asthma, respiratory infection (e.g. pneumonia, pneumocystits carinii, cystic fibrosis, and respiratory syncytial virus) as well as for the treatment of serous otitis media (glue ear).

Other features of the invention will become apparent in the course of the following descriptions of exemplary embodiments which are given for illustration of the invention and are not intended to be limiting thereof.

EXAMPLES

Example 1—Preparation of Formulations According to the Invention

A mixture of DPPC:POPG Na in a 1:1 ratio, SPC-33(leu) and oxidized Mini-B(leu) was dissolved in chloroform/ethanol 98:2 (v/v). The solvent was evaporated and the resulting powder is subsequently hydrated in 0.9% w/v NaCl aqueous solution under stirring and in the presence of 10 mmol of a phosphate-buffered saline, to give a surfactant concentration of 80 mg/ml. The unitary composition of formulation 1 is reported in Table 1.

TABLE 1

Formulation 1

| Ingredient | % | Conc |
|---|---|---|
| SP-C33(leu) | 1.49 | 1.2 mg/ml |
| oxidized-Mini-B(leu) | 0.2 | 0.16 mg/ml |
| DPPC | 48.7 | 39.32 mg/ml |
| POPG Na | 48.7 | 39.32 mg/ml |
| $Na_2HPO_4$ heptahydrate | | 0.58 mg/ml |
| $NaH_2PO_4$ monohydrate | | 1.55 mg/ml |
| NaCl | | 9 mg/ml |
| Water q.b. | | |

The pH turned out to be 6.9±0.2. The viscosity of said formulation was about 9 cP at 25° C. and about 7 cP at 37° C.

Similar formulations were obtained by replacing PBS either with 10 mmol TRIS HCl or a 10 mmol phosphate buffer made of $Na_2HPO_4$ dihydrate, and $NaH_2PO_4$ dihydrate.

Example 2—Stability Studies Carried Out on the Formulations of Example 1

The stability of the formulation filled in 3 ml amber vials was evaluated at 5° C. The assay of SPC-33(leu), oxidized Mini-B(leu) and the two phospholipids were determined by HPLC. The total impurities were also determined by HPLC and expressed as percentage. The total impurities comprise the lyso forms lyso-PC and lyso-PG forming during storage.

The following parameters were also tested: pH, viscosity and particle size of the vesicles. To determine the viscosity, the sample was left to recover at 37° C.

The results are reported in Table 2.

The formulation of the present invention turned out to be physically and chemically stable for at least 18 months at 5° C. In fact, no significant variation in the assay of the four components was observed within the accepted experimental error (±5%).

The total amount of lyso-PC+lyso-PG was well lower than 5.0%.

Furthermore, the viscosity remained substantially unchanged within the limits of experimental error and no significant increase was observed.

Similar findings were observed with the formulation 2.

TABLE 2

Stability of formulation 1

| Formulation 1 | pH | Viscosity mPas | Particle size (micron) | SP-C33(leu) mg/ml % initial | Mini-B(leu) mg/ml % initial | DPPC mg/ml % initial | POPG Na mg/ml % initial | Total impurities (%) |
|---|---|---|---|---|---|---|---|---|
| Specification | 6.5-7.5 | <25 mPas | 1.0-25 d(v, 50) 8-15 | 1.02-1.32 | 0.136-0.176 | 33.42-43.25 | 33.42-43.25 | |
| Initial (t = 0) | 6.9 | 7.2 | — | 1.15  100.0 | 0.158  100.0 | 39.55  100.0 | 38.33  100.0 | 0.50 |
| t = 3 months | 6.9 | 5.4 | — | 1.15  100.0 | 0.160  101.3 | 39.07  98.8 | 38.87  101.4 | 0.61 |
| t = 6 months | 6.9 | 6.8 | — | 1.14  99.1 | 0.157  99.4 | 39.15  99.0 | 39.06  101.9 | 1.03 |
| t = 12 months | 6.9 | 8.1 | — | 1.15  100.0 | 0.151  95.6 | 38.16  96.5 | 38.64  100.8 | 0.94 |
| t = 18 months | 6.9 | 6.9 | complies | 1.15  100.0 | 0.151  95.6 | 38.96  98.5 | 38.45  100.3 | 2.60 |

Example 3—In Vivo Activity of the Formulation 1

The in vivo activity of the formulation 1 of Example 1 was tested at t=0 and after 18 months at 5° C. It was assayed in premature newborn rabbits, obtained by hysterectomy at the gestational age of 27 days. The experiments are performed without applying a positive end expiratory pressure (PEEP).

Animals receiving Curosurf® serve as positive controls and non-treated littermates as negative controls.

All surfactant preparations are administered at a concentration of 80 mg/ml and at a standard dose of 2.5 ml/kg.

The immature new-born rabbits were ventilated in parallel with a standardized sequence of peak insufflation pressures. To open up the lungs, pressure is first set at 35 $cmH_2O$ for 1 min. After this recruitment manoeuvre, pressure was lowered to 25 $cmH_2O$ for 15 min and further on to 20 and 15 cm $H_2O$.

Finally, pressure was increase again to 25 cm $H_2O$ for 5 min, after which the lungs were ventilated for additional 5 min with nitrogen and then excised for gas volume measurements.

Both tidal volumes and lung gas volumes, expressed as ml/kg, were measured and turned out be similar at t=o and after 18 months at 5° C.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

---

The invention claimed is:

1. A pharmaceutical formulation in foil of aqueous suspension, comprising:
   (a) from 1.02 to 1.32 mg/ml of a polypeptide analog of the native surfactant protein SP-C with the sequence IPSSPVHLKRLKLLLLLLLLILLLILGALLLGL (SEQ. ID:NO.1);
   (b) from 0.136 to 0.176 mg/ml of a polypeptide analog of the native surfactant protein SP-B with the sequence CWLCRALIKRIQALIPKGGRLLPQLVCRLVLRCS (SEQ. ID:NO. 2);
   (c) from 33.42 to 43.25 mg/ml of 1,2-dipalmitoyl-sn-glycero-3-phosphocholine (DPPC);
   (d) from 33.42 to 43.25 mg/ml of the sodium salt of 1-palmitoyl-2-oleyl-sn-glycero-3-phosphoglycerol (POPG Na);
   (e) from 0.6 to 3.0 mg/ml of a buffer agent selected from the group consisting of tris(hydroxymethyl)aminomethane hydrochloride and a phosphate-buffer; and
   (f) a tonicity agent in an amount sufficient to provide an osmolarity of from about 250 to about 400 mosm/l;
   which has a pH of 6.4 to 7.6,
   wherein said formulation exhibits a viscosity of less than 10 mPas at 37° C. after storage for 18 months at 5° C.

2. The formulation according to claim 1, wherein the concentration of the polypeptide of SEQ. ID:NO.1 is 1.2 mg/ml, the concentration of the polypeptide of SEQ. ID:NO.2 is 0.16 mg/ml, and the concentration of both DPPC and POPG Na are 39.32 mg/ml.

3. The formulation according to claim 1, which has a pH of 6.5 to 7.5.

4. The formulation according to claim 1, which has an osmolarity of from about 250 to about 400 mosm/l.

5. The formulation according to claim 4, which has an osmolarity of from 280 mosm/l to 380 mosm/l.

6. The formulation according to claim 1, wherein said tonicity agent is selected from the group consisting of dextrose, mannitol, sorbitol potassium chloride, and sodium chloride.

7. The formulation according to claim 6, wherein said tonicity agent is sodium chloride.

8. The formulation according to claim 1, further comprising a corticosteroid.

9. The formulation according to claim 8, wherein said corticosteroid is beclometasone dipropionate or budesonide.

10. A method for the treatment of respiratory distress syndrome or another disease related to a surfactant-deficiency or dysfunction, said method comprising administering to a subject in need thereof an effective amount of a formulation according to claim 1.

11. The method according to claim 10, wherein said another disease is RDS in adults, meconium aspiration syndrome, or broncho-pulmonary dysplasia (BPD).

12. The formulation according to claim 1, which exhibits a viscosity of less than 8 mPas at 37° C.

13. The formulation according to claim 1, which exhibits a viscosity of less than 10 mPas at 25° C.

14. The formulation according to claim 1, wherein the viscosity does not increase above 10 mPas at 37° C. after storage for 18 months at 5° C.

* * * * *

```
                        SEQUENCE LISTING

<160> NUMBER OF SEQ ID NOS: 2

<210> SEQ ID NO 1
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 1

Ile Pro Ser Ser Pro Val His Leu Lys Arg Leu Lys Leu Leu Leu Leu
1               5                  10                  15

Leu Leu Leu Leu Ile Leu Leu Leu Ile Leu Gly Ala Leu Leu Leu Gly
            20                  25                  30

Leu

<210> SEQ ID NO 2
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: DISULFID
<222> LOCATION: (1)..(33)
<223> OTHER INFORMATION: Intramolecular disulfide linkage may be present
      or absent
<220> FEATURE:
<221> NAME/KEY: DISULFID
<222> LOCATION: (4)..(27)
<223> OTHER INFORMATION: Intramolecular disulfide linkage may be present
      or absent

<400> SEQUENCE: 2

Cys Trp Leu Cys Arg Ala Leu Ile Lys Arg Ile Gln Ala Leu Ile Pro
1               5                  10                  15

Lys Gly Gly Arg Leu Leu Pro Gln Leu Val Cys Arg Leu Val Leu Arg
            20                  25                  30

Cys Ser
```